US00PP26788P2

(12) United States Plant Patent
Hurd

(10) Patent No.: US PP26,788 P2
(45) Date of Patent: May 31, 2016

(54) *HEUCHERA* PLANT NAMED 'BLACKBERRY ICE'

(50) Latin Name: ***Heuchera* hybrid**
Varietal Denomination: Blackberry Ice

(71) Applicant: Kevin A. Hurd, Chicago, IL (US)

(72) Inventor: Kevin A. Hurd, Chicago, IL (US)

(73) Assignee: Walters Gardens, Inc., Zeeland, MI (US)

( * ) Notice: Subject to any disclaimer, the term of this patent is extended or adjusted under 35 U.S.C. 154(b) by 268 days.

(21) Appl. No.: 13/998,788

(22) Filed: Dec. 6, 2013

(51) Int. Cl.
*A01H 5/12* (2006.01)

(52) U.S. Cl.
USPC ..... Plt./440

(58) Field of Classification Search
USPC ..... Plt./440
See application file for complete search history.

*Primary Examiner* — June Hwu

(57) ABSTRACT

The new and distinct hybrid plant of *Heuchera* named 'Blackberry Ice' with foliage color that changes throughout the year emerging in the spring as iridescent purple with lighter pinkish purple interveinal distal regions with dark greenish purple veins. Foliage then progresses to intense silvering with dark green with purple undertones and by late season and into winter intensifying the purple and decreasing the silvery regions between the veins. The very light pink campanulate flowers appear on a branched panicle effective over a long period. The new plant is vigorous, compact in habit and tolerates heat and humidity well.

1 Drawing Sheet

Botanical denomination: *Heuchera* hybrid.
Cultivar designation: 'Blackberry Ice'.

BACKGROUND OF THE INVENTION

The present invention relates to a new and distinct cultivar of Coral Bells in the Saxifragaceae family and given the cultivar name of 'Blackberry Ice'. *Heuchera* 'Blackberry Ice' was hybridized by Kevin A. Hurd on Jul. 3, 2009 at a nursery in Zeeland, Mich., USA. The seed or female parent was 'Plum Royale' U.S. Plant Pat. No. 20,935 and the pollen or male parent was a proprietary unreleased hybrid known as Heu-08-04-01 (not patented) ('Pinot Noir' U.S. Plant Pat. No. 20,434×'Mocha' U.S. Plant Pat. No. 18,386). 'Pinot Noir' has both *Heuchera brizoides* and *H. villosa* in the parentage and 'Mocha' is a selection of *H. villosa*. *Heuchera* 'Blackberry Ice' was first selected in the spring of 2010 and passed final evaluation in the fall of 2011 from among thousands of other seedlings from the same cross and hundreds of other crosses. *Heuchera* 'Blackberry Ice' was has been asexually propagated by division at the same nursery in Zeeland, Mich. and by careful tissue culture propagation, and the resultant plants have remained stable and exhibit the same characteristics as the original plant for multiple generations.

BRIEF SUMMARY OF THE INVENTION

In comparison to the female parent, 'Plum Royale', the new plant has broader vein color width, more acute leaf lobe apices.

The nearest comparison varieties are *Heuchera* 'Plum Royale' U.S. Plant Pat. No. 20,935 and 'Plum Pudding' (not patented). *Heuchera* 'Plum Royale' flowers are more pink and the flowers of 'Plum Pudding' are more cream-colored than the light pink of 'Blackberry Ice'. The foliage of 'Plum Pudding' is less intense purple and more silver than the new plant with less of the contrasting deep green in the veins, and 'Plum Royale' has foliage of more cupped downward, have less contrasting green with the purple compared with 'Blackberry Ice'. In comparison to the male parents and grandparents, *Heuchera* 'Blackberry Ice' has more intense purple and silver in the foliage and whiter flowers.

*Heuchera* 'Blackberry Ice' differs from its parents as well as all other Coral Bells known to the applicant in the following combined traits:

1. The foliage color of 'Blackberry Ice' changes throughout the year emerging iridescent purple with lighter pinkish purple interveinal distal regions with dark greenish purple surrounding the veins.
2. Foliage then progresses to intense silvering with purple undertones and by late season and into winter intensifying the purple and decreasing the silvery regions between the veins.
3. The very light pink campanulate flowers appear on a branched panicle effective over a long period.
4. The new plant is vigorous, compact in habit and tolerates heat and humidity.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
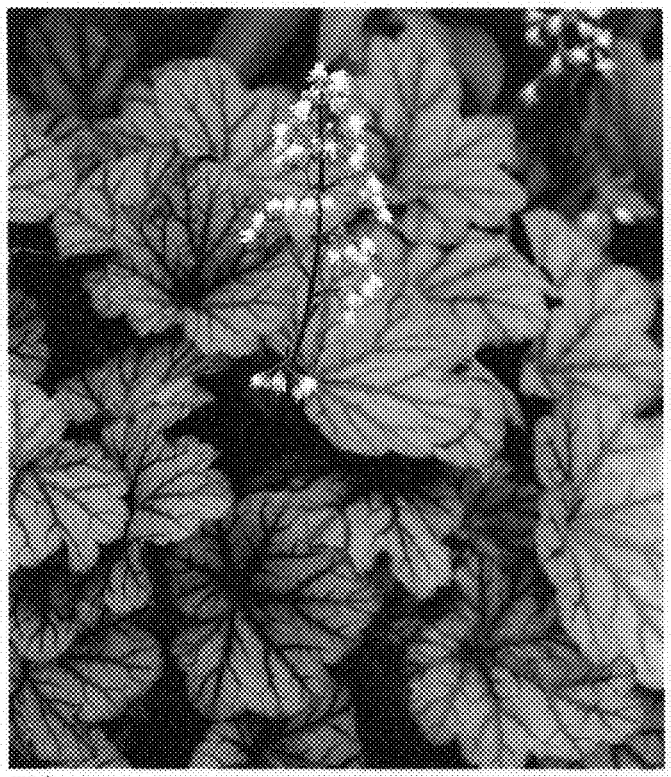
FIG. 1 shows a close-up of the foliage of the new plant with early flowering.
Figure 2:
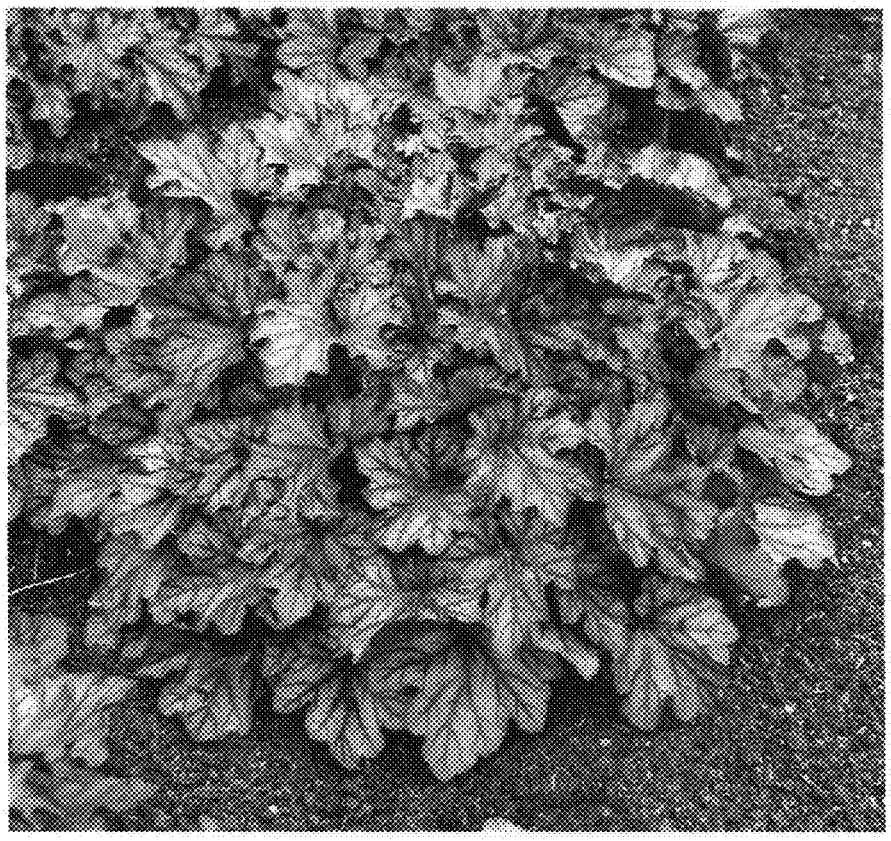
FIG. 2 shows a one-year old plant with late winter or early spring foliage.

The following description is based on a two-year old plant growing in a lightly shaded greenhouse in Zeeland, Mich., USA. A one-year old plant grown in a shaded trial garden with supplemental water and fertilizer was also used for further descriptions of late winter or early spring foliage colors. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage:

*Female* (*seed parent*).—'Plum Royale' U.S. Plant Pat. No. 20,935.

*Male* (*pollen*).—Heu-08-04-01 (a non-patented, proprietary, unreleased hybrid of 'Pinot Noir' U.S. Plant Pat. No. 20,434×'Mocha' U.S. Plant Pat. No. 18,386).

Plant habit: Hardy herbaceous perennial with basal rosette of foliage; mounded foliage about 26 cm tall and 45 cm in diameter.

Roots: Fibrous, finely branched.

Growth rate: Rapid, rooting from cutting in two weeks and finishing in three-liter container in about 3 months.

Foliage: Cordate, serrate, sparsely hirsutulous, palmately lobed with up to seven main lobes each having three or more sub-lobes; blade up to about 14.5 cm long and 13.5 cm wide, average about 10.5 cm long and 10.0 cm wide; undulate, being pinched together at abaxial indentations of lobes in such a way that the adaxial surface is elevated by up to 1.5 cm, and occasionally lightly concavely cupped upward; leaf color is variable with season.

Leaf color: Spring young emerging leaves adaxial nearest RHS N186C with little or no silver, spring young emerging leaves abaxial between RHS N186C and RHS N186D; mid-season flowering time leaves adaxial surrounding veins nearest RHS N186A, silvering between veins between RHS N187B and RHS N187C with some extra tinting of iridescent purple nearest RHS N77B; abaxial mid-season leaves between RHS N186B and RHS N186C; adaxial winter and early spring leaves surrounding veins nearest RHS N186A with area between the veins between RHS N77B and RHS 77C; abaxial winter and early spring leaves nearest RHS N186C; winter shaded leaves adaxial surrounding veins nearest RHS 139A and area between veins between RHS 191C and RHS 189C with margin tinting of nearest RHS 187B; winter shaded leaves abaxial nearest RHS 183B with tinting of RHS N77B and RHS 194B.

Leaf margin: Dentate to hirsutulous with lobules finely fimbricate to mucronate at apices.

Leaf apex: Rounded, mucronate.

Leaf base: Cordate, auriculate with overlapping lobes.

Leaf surface: Sparsely hirsutulous abaxial and adaxial; adaxial slightly vernicose when young in spring, matte when mature; abaxial vernicose all season.

Leaf quantity: Dense, about 50 per plant.

Veins: Palmate, hirsutulous; ridged abaxial.

Vein color: On emerging spring foliage adaxial nearest RHS 186A at base and nearest RHS N186C distally with abaxial nearest RHS N186C; mid-season flowering time adaxial between RHS 183C and RHS 183D proximally and distally nearest RHS N186C, mid-season flowering time abaxial nearest RHS N77B; winter adaxial blended between RHS 177C and RHS 182C proximally nearest petiole and between RHS 139A and RHS 139B distally, with abaxial nearest RHS N77B.

Petiole: Cylindrical, sparsely hirsutulous; up to about 17 cm long and 3 mm wide.

Petiole color: Distally RHS 182C and RHS 148C with slight tinting of nearest RHS 185B proximally near base of plant where more shaded, between RHS N186D and RHS N186C in higher light.

Inflorescence: Mostly-vertical open panicle, medium density of flowers; one panicle per main division, about 10 per plant; about 150 to 175 flowers per panicle; branches held at about 20 to 30 degree angle from vertical peduncle; lower branches about 8 cm long and decreasing distally and about 0.5 mm diameter; panicle head about 9 cm across and 38 cm tall; flowering starting in late spring to early summer lasting for about 3 weeks; no significant fragrance detected.

Peduncle: Stiff, cylindrical, densely hirsutulous, about 55 to 60 cm long and 3 mm in diameter at base.

Peduncle color: Between RHS 187A and RHS N187A proximally and nearest RHS 187B distally.

Pedicel: Cylindrical, hirsutulous, about 2.5 mm long and 0.5 mm diameter, curving slightly downwards to less than 30 degrees from horizontal.

Pedicel color: Nearest RHS 138B.

Bracts: At panicle main nodes incised to five lobed, about 10 mm long and 2.0 mm wide decreasing distally, with acute apices and base sessile and truncate; color nearest RHS 187B.

Buds one day prior to opening: Ellipsoid, about 4.0 mm long and 2.5 mm diameter; hirsutulous; facing semi-downwards less than 30 degrees from horizontal.

Bud color: Base nearest RHS 138B with tinting to portions nearest RHS 187B; distal sepal portions nearest RHS 138A with portions between of nearest RHS N155C with tinting nearest RHS 187B.

Flower: Perfect, campanulate, actinomorphic, about 9.0 mm long and 5.0 mm in diameter at face; individual flowers lasting about 4 days on plant or as cut flower.

Calyx: Five, apex acute, base fused in proximal half to form hypanthium; about 4.0 mm long and 2.5 mm wide; facing semi-downwards about 15 to 30 degrees from horizontal when initially opened.

Calyx color: In the abaxial middle nearest RHS N155D with apical tip about 0.5 mm long nearest RHS 143C and base 3.0 mm a mixture of between RHS 139B and RHS 139C with tinting of nearest RHS 184C; in the adaxial middle near white, lighter than RHS N155D with apical tip about 0.5 mm long nearest RHS 143C and a base of nearest RHS 186D with tinting of RHS N144D.

Petals: Five, oblanceolate, acute apex and tapered base, entire, about 4.0 mm long and 1.0 mm wide in middle.

Petal color: White, lighter than RHS 155D.

Androecium:

*Filaments*.—Five, thin, about 5.0 mm long and less than 0.5 mm diameter; color white, lighter than RHS155D.

*Anthers*.—Color nearest RHS N163B.

*Pollen*.—Color nearest RHS 16C.

Gynoecium: Two-beaked; bifid style with pistil split at ovary; 6 mm long.

*Ovary*.—Half-inferior, about 3.0 mm long and 2.5 mm diameter, pointed apex ending in style, base rounded, color nearest RHS 144C.

*Style*.—Two, split apart at apex of ovary; about 5.0 mm long and less than 0.5 mm diameter; slightly curving splitting apart about 2.0 mm at distal region; color white, lighter than RHS 155D before fertilization and afterward nearest RHS 187D with an apex white, lighter than RHS 155D.

*Stigma*.—Smaller than 0.5 mm diameter, globose; color lighter than RHS 145D.

Fruit: Two-beaked capsule, about 6 mm long and 3 mm in diameter at widest portion; color nearest RHS 199A when mature.

Seed: Ovoid, less than 1 mm long and wide; color black, nearest RHS 202A.

Disease and pest tolerance: The new plant grows best with ample moisture and drainage in either sun or shade. It is more tolerant of hot and humid environments than typical Coral Bells. Cold hardy from USDA zones 4 to 9. Other resistance and tolerance outside of that normal for *Heuchera* is not known.

I claim:

1. The new and distinct Coral Bells plant named *Heuchera* 'Blackberry Ice' as herein described and illustrated with foliage changing colors throughout the seasons, comprising very light pink flowers and with improved heat and humidity tolerance suitable for landscaping or as cut flower or foliage decoration.

* * * * *